United States Patent [19]

Vanasco et al.

[11] 4,069,716
[45] Jan. 24, 1978

[54] APPARATUS AND METHOD FOR USE IN DETERMINING CONDITIONS RELATED TO A PLANT

[75] Inventors: Salvatore Vanasco, Huntington, N.Y.; Wayne Chou, Stamford, Conn.

[73] Assignee: LMC Data, Inc., Ronkonkoma, N.Y.

[21] Appl. No.: 655,443

[22] Filed: Feb. 5, 1976

[51] Int. Cl.² .................................... G01N 33/18
[52] U.S. Cl. ............................ 73/432 R; 73/73; 324/65 P; 356/227
[58] Field of Search ............ 73/432 R, 73; 356/213, 356/227, 72; 324/30 R, 65 P

[56] References Cited

U.S. PATENT DOCUMENTS

| | | | |
|---|---|---|---|
| 2,015,431 | 9/1935 | McIlvaine | 356/227 X |
| 2,793,527 | 5/1957 | Turner, Jr. et al. | 73/73 |
| 3,019,384 | 1/1962 | Wayne | 73/73 X |
| 3,117,442 | 1/1964 | Brooks | 73/73 |
| 3,779,651 | 12/1973 | Gunlock | 356/213 |
| 3,806,797 | 4/1974 | Harvey | 324/30 R |
| 3,876,312 | 4/1975 | Harcrow, Jr. | 356/227 X |
| 3,881,873 | 5/1975 | Klowden | 73/73 X |

FOREIGN PATENT DOCUMENTS

| | | | |
|---|---|---|---|
| 862,420 | 2/1971 | Canada | 73/432 R |
| 2,314,902 | 3/1973 | Germany | 73/73 |

*Primary Examiner*—Richard C. Queisser
*Assistant Examiner*—Joseph W. Roskos
*Attorney, Agent, or Firm*—Blum, Moscovitz, Friedman & Kaplan

[57] ABSTRACT

A method and apparatus for use in detecting conditions related to a plant are disclosed. More particularly, in accord with the invention, in the method and apparatus are provided a first sensing means for generating an electrical signal corresponding to the light level in the area surrounding a plant, an indication means comprising a meter for providing an indication or reading corresponding to the electrical signal generated by the sensing means, and a reference source in the form of a chart or table for relating the aforesaid indication or reading to a preselected reading associated with the particular plant.

In a further aspect of the invention, a second sensing means is additionally provided for sensing another condition of the plant and a coupling means is provided for selectively coupling the first and second sensing means to the meter of the indication means. Moreover, in this form of the invention, a second reference source is provided for presenting reference readings corresponding to the condition being sensed by the second sensing means.

Also disclosed is a housing for the apparatus which is designed to have storage capabilities and to permit easy use thereof.

13 Claims, 8 Drawing Figures

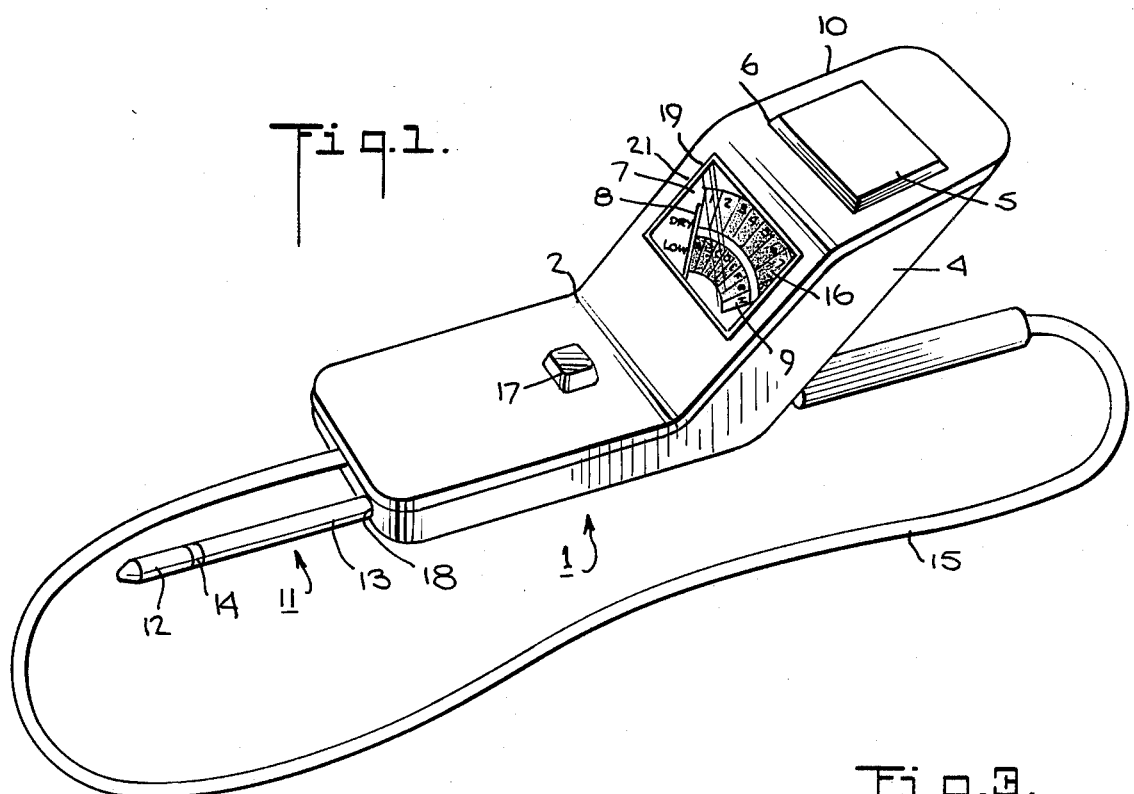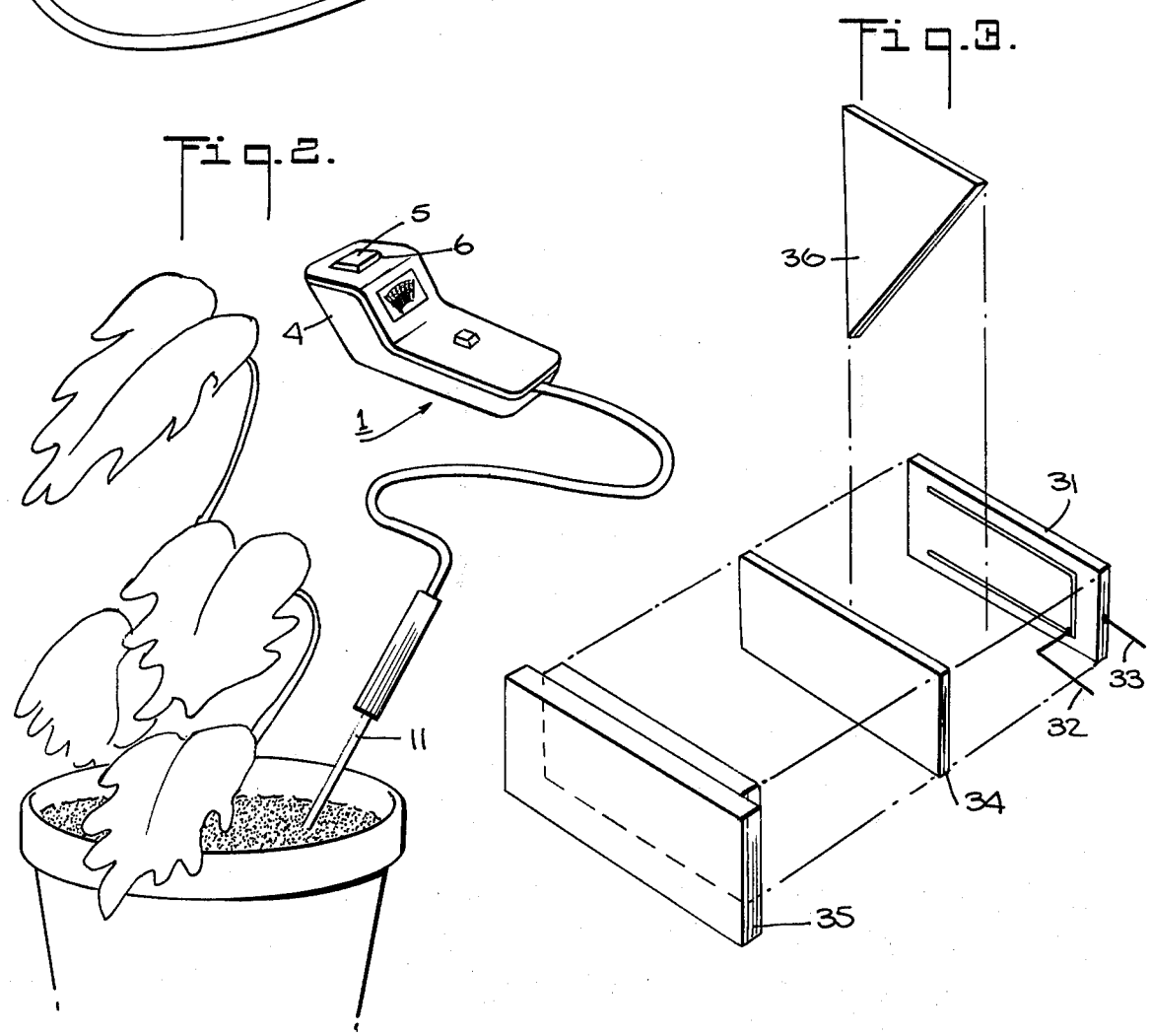

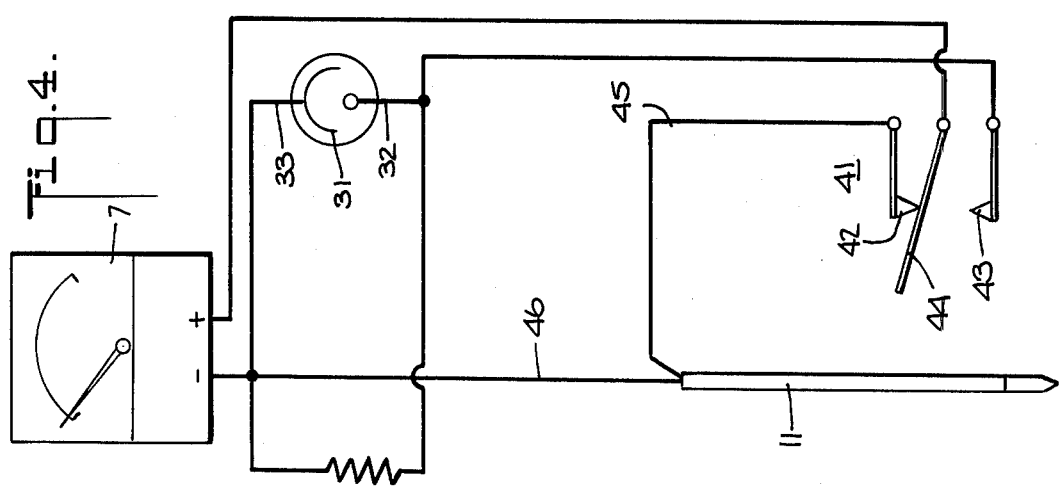
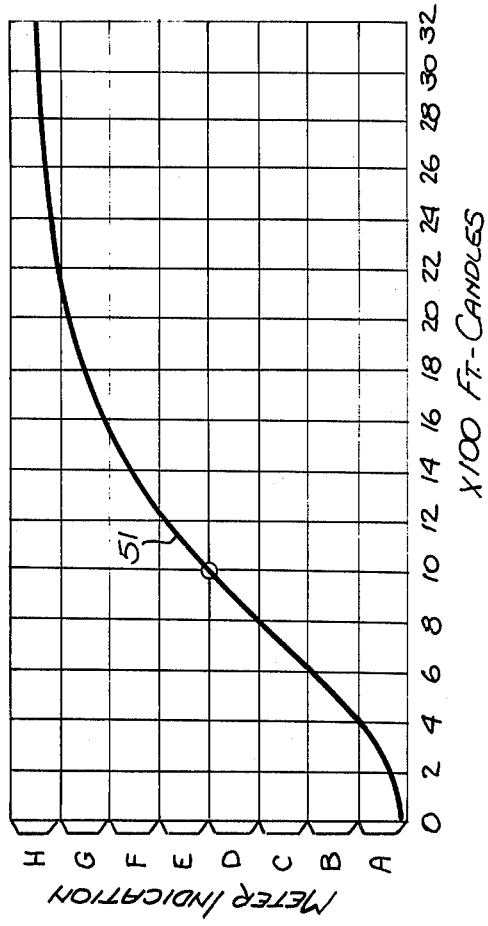
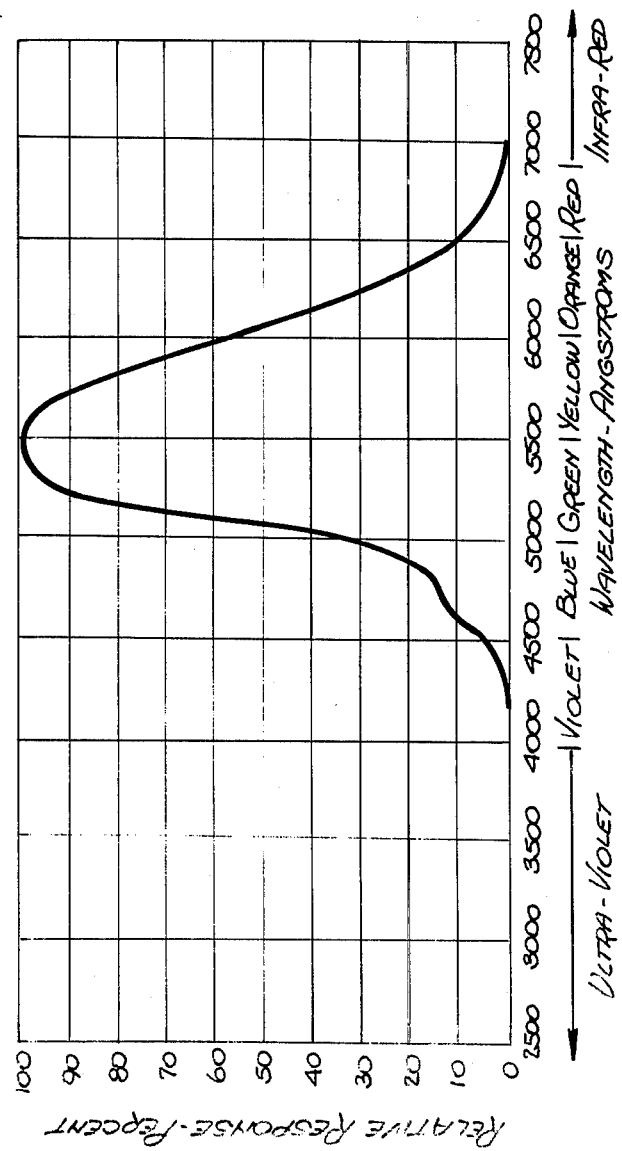

Fig. 7.

| Category or Type of Plant | Meter Reading Below Which Plant Needs Additional Light |
|---|---|
| Zebra Plant (Aphelandra) | E |
| Citrus (Orange, Lemon, Lime) | G |
| Dracaena Species | C |

Fig. 8.

| Category or Type of Plant | Meter Reading Below Which Plant Needs Additional Water |
|---|---|
| Zebra Plant (Aphelandra) | 6-7 |
| Citrus (Orange, Lemon, Lime) | 3-4 |
| Dracaena Species | 6-7 |

APPARATUS AND METHOD FOR USE IN DETERMINING CONDITIONS RELATED TO A PLANT

BACKGROUND OF THE INVENTION

The widespread use of plants to decorate today's homes has created a need for aids to help the homeowner in caring for his plants. This need stems from the fact that the typical homeowner knows little, if anything, about detecting the conditions required to stimulate continued and healthy growth of his newly acquired plants. Thus, for example, the two main conditions for stimulating proper plant growth, i.e., the water and lighting conditions to which a plant is subjected are not ordinarily conditions which a homeowner can readily detect. This is especially true with respect to lighting conditions, since it is virtually impossible to accurately gauge by eye the degree of sunlight reaching a plant in a particular location. While subjecting a plant to different lighting conditions may be a way to arrive at an appropriate lighting condition, this method may often result in death to the plant before a suitable condition is found.

The above difficulties encountered by the homeowner are further compounded by the fact that there is now an extremely large variety of plants being sold for home use. Thus, the homeowner desiring some variety in his plant decor is faced with having to detect not only the above mentioned conditions associated with one type of plant, but the conditions, which most assuredly will be different, for other types of plants as well.

In copending application Ser. No. 520,862, filed on Nov. 4, 1974, there is disclosed an apparatus for use with plants which offers a partial solution to the homeowner's dilemma. More particularly the aforesaid apparatus comprises a meter which generates a reading associated with the water condition of the soil of a plant and includes means for relating this reading to a normal or desirable reading for the particular plant. While such apparatus thus substantially solves the homeowner's problem of detecting the water condition of his plants, it is of no help with respect to the lighting and pH conditions, which also, as above indicated, must be accurately controlled if healthy plant life is to be maintained.

It is, therefore, an object of the present invention to provide an apparatus for aiding the homeowner in proper caring of his plants.

It is a further object of the present invention to provide an apparatus usable by a homeowner for generating indications corresponding to the lighting conditions to which his plants are being subjected and to provide a means for determining whether the generated indications indicate satisfactory conditions for plant growth.

It is also an object of the present invention to provide an apparatus which has the capability of selectively providing indications corresponding to both the water and lighting conditions of a plant.

It is a further object of the present invention to provide an apparatus having the aforesaid dual capability which is designed to be as inexpensive as possible.

SUMMARY OF THE INVENTION

The above and other objectives are accomplished in accordance with the principles of the present invention by an apparatus and method for use with plants in which there are provided a first sensing means for generating an electrical signal corresponding to the light level in the area surrounding a plant, an indication means comprising a meter for providing an indication or reading corresponding to the electrical signal generated by the sensing means and a reference source in the form of a chart or table for relating the aforesaid indication or reading to a preselected reading associated with the particular plant. The aforesaid preselected reading corresponds to a light level or lighting condition which is suitable for the particular plant. Thus, if the reading on the meter is below this preselected reading, the homeowner is immediately informed that the particular plant is receiving too little light. He can then adjust the lighting conditions until a condition is reached in which the reading being taken is the same as the preselected reading. At this point, the homeowner is now assured that the particular plant is receiving the appropriate level of light.

In a further aspect of the invention, a second sensing means is additionally provided for sensing another condition of the plant and coupling means is provided for selectively coupling the first and second sensing means to the meter of the indication means. In this way, the same meter can be used to generate readings corresponding to the lighting condition as well as the aforesaid other condition of the plant. Additionally, in this form of the invention, another reference source, also in the form of a chart or table, is provided for relating the meter reading derived from the second sensing means to a preselected reference reading associated with the condition of the plant being sensed.

More particularly, in the embodiment disclosed, the aforesaid coupling means is in the form of a controllable switch for switchably disconnecting one and connecting the other of different sensing means to the meter. Moreover, in such embodiment the other condition being sensed is the water condition or moisture content of the soil of the plant, and the second sensing means is in the form of a slender probe having spaced electrodes comprised of different metals which when inserted into the soil of a plant generates a natural current through voltaic electrolytic action which is indicative of the moisture content of the soil.

In still a further aspect of the invention, the above embodiment of the present apparatus having the dual capability of sensing the light and soil conditions of a plant is additionally provided with a housing which is configured to permit easy operation of the apparatus and ready storage of the probe of the water sensing means thereof. In particular, the housing includes a relatively thin, elongated bottom housing portion adapted to be gripped by the user and from whose upper surface protrudes a pressable knob for operating the switch controlling the coupling of the two sensing means. The aforesaid bottom housing portion also includes a slot or aperture which extends through its length and into which the probe of the water sensing means is stored when not in use. Additionally, the housing further includes at one end of the bottom portion an upwardly extending portion having an upper surface which includes an aperture or window through which light is coupled onto the light sensing means of the apparatus. This upwardly extending portion also has a slanted side having an aperture through which the face of the meter of the apparatus can be readily observed.

BRIEF DESCRIPTION OF THE DRAWINGS

The above and other features and aspects of the present invention will become more apparent upon reading the following detailed description in conjunction with the accompanying drawings, in which:

FIG. 1 shows an apparatus in accordance with the principles of the present invention;

FIG. 2 illustrates the apparatus of FIG. 1 being used to detect the conditions to which a plant is being subjected;

FIG. 3 shows the light sensing means of the apparatus of FIG. 1 in greater detail;

FIG. 4 is a schematic showing the electrical connections of the apparatus of FIG. 1;

FIG. 5 shows a typical characteristic relating the calibrated segments of the light scale portion of the apparatus of FIG. 1 to particular light level ranges;

FIG. 6 illustrates a typical spectral characteristic for the light sensing means of FIG. 3; and FIGS. 7 and 8 show typical light and water reference sources, respectively, of the apparatus of FIG. 1.

DETAILED DESCRIPTION

FIG. 1 shows an apparatus 1 for use in determining conditions related to plant life in accordance with the principles of the present invention. More particularly, apparatus 1 comprises a housing 2 having a relatively thin, elongated bottom portion 3 at one of whose ends is situated and upwardly extending housing portion 4. The housing portion 4 houses a light sensing means 5 which is arranged therein to receive light through an aperture 6 situated in the upper surface 10 of the housing portion.

Electrically connected to the light sensing means 5 and also housed within the portion 4 of the housing 2 is a simple galvanic meter 7. The meter 7 provides a visual indication of the level or intensity of light being sensed by sensing means 5 through the location of the pointer 8 of the meter along the lower scale 9 on the face of the meter. The face of the meter is readily visible through an aperture 19 in the slanted sidewall 21 of the portion 4.

As shown, the scale 9 is segmented into 8 segments A to H. Each of these segments corresponds to a specific range of light levels, with the segment A corresponding to the lowest range and the segment H the highest range of such levels. FIG. 5 shows a typical characteristic 51 relating the segments A to H of scale 9 to their corresponding ranges of light levels.

As can be appreciated, the number of segments into which scale 9 is divided is a function of the degree of accuracy required in determining the light level. Over a given overall range, the larger the number of segments the greater will be the accuracy. In the present case, the accuracy required, and, thus, the number of segments employed for scale 9 is a function amongst other things, of the ranges of the light levels considered suitable for the plants expected to be tested.

In further accord with the invention, the apparatus 1 is further provided with a reference source developed by relating each of the meter readings on the scale 9 to the light levels considered suitable for different varieties of plants. As shown in FIG. 7, the reference source 71 of apparatus 1, is in the form of a chart which lists in one column different plants and in an adjacent column the corresponding meter readings on scale 9 indicative of acceptable light levels for such plants.

As can be appreciated, the reference source 71 can be developed by relating the known acceptable light levels for different plants to the characteristic for the segments of scale 9 shown in FIG. 5. In particular, by plotting such acceptable levels on the curve 61, the corresponding segments A to H in which such levels fall can be determined. Once the latter segments are determined, they can be used on the reference source 71 to indicate the meter readings on scale 9 below which readings for their corresponding plants would indicate unacceptable light levels.

As can also be appreciated, the source 71 can be as extensive as desired with respect to the number or types of plants listed. For a small number of plants the source can be made into a small card which can be adhered directly to the outer surface of the casing 2.

FIG. 3 shows schematically the light sensing means 5 of apparatus 1 in greater detail. As shown, it comprises a photocell 31 to which are connected electrical leads 32 and 33. In front of the photocell 31 is a conventional color correction filter 34 which itself is fronted by a conventional cosine correction lens 35. A calibration wedge 36 comprising opaque black paper is also included in the means 5 between the filter 34 and the photocell 31.

With the means 5 configured as above, its spectral sensitivity will closely approximate that of the eye, as shown by the light sensitivity characteristic 61 in FIG. 6.

The operation of the apparatus 1 in testing whether a plant is receiving a suitable amount of light is carried out, as shown in FIG. 2, by placing the housing portion 4 and, thus, the aperture 6 therein, adjacent the plant so that the sensing means 5 is receiving substantially the same light level as the plant. The meter reading obtained on scale 9 is then read and compared to the reference reading on the source 71 corresponding to the particular plant. If the reading is below the reading on the chart, it is an indication that the plant needs more light and should be moved to a position where it can receive increased light.

It should be noted that the source 71 can also be provided with reference meter readings for the listed plants beyond which the plants are considered to be receiving too much. In such case, if the meter reading for a particular plant is above the latter reference reading for such plant, it will be an indication that the plant is receiving too much light and should be moved to a position where the light level is decreased.

While the apparatus 1 can thus provide an indication of whether a plant is receiving an appropriate amount of light, it is further adapted, in accordance with the principles of the invention, to permit another condition of the plant to be determined with the addition of only a minimum number of extra components and, in particular, through the use of the same meter 7 employed to detect the lighting condition of the plant. More specifically, this is accomplished, in accord with the invention, as shown in FIG. 4, by providing the apparatus 1 with a selective coupling means or switch 41 through which the photocell 31 of light sensitive means 5 is coupled to the meter 7. The aforesaid switch is designed so as to be able to selectively disconnect the photocell 31 from the meter 7 and connect thereto another sensing means 11 which is sensing another condition of the plant.

As shown, the switch 41 comprises two stationary contacts 42 and 43 and a movable contact 44 which is connected to the plus terminal of the meter 7 and which can be selectively brought into contact with the contacts 42 and 43. The contact 42 is, in turn, connected to one output lead 45 of the sensing means 11, while the other output lead 46 of such means is connected to the minus terminal of the meter 7. The contact 43, on the other hand, is connected to the lead 32 of the photocell 31 whose other lead 33 is also connected to the minus terminal of the meter 7. As can be appreciated, therefore, movement of the contact 44 into contact with contact 42, as is the case shown, places the sensing means 11 in the meter circuit so the latter provides a reading corresponding to the condition being sensed by sensing means 11. On the other hand, movement of the contact 44 into contact with the contact 43 places the photocell 31 into the meter circuit, thereby causing the latter to provide a reading corresponding to the light level being detected by the cell in the manner described above.

In the present illustrative embodiment, the sensing means 11 is in the form of a probe for detecting the water condition of the soil of a plant, and the apparatus 1 is further adapted so as to be able to relate the moisture condition detected by probe 11 to the appropriate water condition of the plant being tested. In particular, such adaptation is in accordance with the teachings of copending patent application Ser. No. 520,862, filed on Nov. 4, 1974.

Specifically, as shown in FIG. 1, the probe 11 includes two electrodes 12 and 13 which are normally insulated from one another via a small plastic plug 14 and which are connected respectively to the two terminals of the meter 7 via lead wires (not shown in FIG. 1) contained within the flexible tubing 15. The electrodes 12 and 13 are comprised of two dissimilar metals such that when placed in an electrolyte there is natural current flow due to voltaic action which is a function of the amount of electrolyte. Thus, when the probe 11 is inserted into the soil of a plant, as shown in FIG. 2, a current is generated by the electrodes which is dependent on the water content or moisture of the soil.

In order to provide a visual indication of the degree of moisture being sensed by probe 11, the meter 7 of apparatus 1 is further adapted to include a second segmented scale 16 whose segments 1-8 correspond to different ranges of moisture content. Moreover, the apparatus 1 is further provided with a second reference source, illustrated as a chart 81 in FIG. 8, developed by relating the readings on the scale 16 to the water required by different varieties of plants.

When determining whether a plant is receiving appropriate moisture, the probe 11 is thus inserted into the soil of the plant and the switch 41 actuated to couple the probe into the circuit of meter 7. The reading on scale 16 is then taken, and this reading is then compared with the reference reading on chart 81 for the particular plant. If the reading on the scale 16 is below the reference reading then the plant is in need of additional water.

As above indicated, apparatus 1 is changed from the condition of being able to determine the water condition of a plant to the condition of being able to determine the lighting condition of a plant by suitable actuation of the switch 41 and, in particular, by suitable movement of the contact 44 of the switch. In the present illustrative embodiment, movement of the aforesaid contact 44 is achieved by use of a pressable knob 17 situated on the upper flat surface of the bottom housing portion 3. In particular, knob 17 is designed so that when in an up position, it places the contact 44 in contact with the contact 42 and, therefore, connects the probe 11 into the meter circuit for taking a moisture reading. Pressing down on the knob 17, on the other hand, moves the contact 44 from the contact 42 to the contact 43 so that the sensing means 5 is now placed in the meter circuit for taking light level readings.

As can be also seen from FIG. 1, the lower housing portion 3 of the apparatus 1 is further adapted to be able to store the probe 11 when the apparatus is not being used. In particular, a longitudinal aperture 18 is provided through the body of the housing portion 3. Thus, when the probe 11 is not being used it can be inserted into the aperture 18 and horizontally stored therein.

It should be also noted, with respect to the configuration of the apparatus 1, that the meter 7 and the sensing means 5 are arranged in the housing portion 4 so as to permit the meter to be easily read during the taking of light readings. In particular, the meter is positioned so that it's face inclines upwardly from the plane of the flat upper surface of the housing portion 3, and the sensing means 5 is positioned so that its upper lens surface inclines downwardly from the plane of the meter face. In the case shown, this has been accomplished by appropriately inclinding the surfaces 21 and 10 of the housing 4 and situating the meter 7 and sensing means 5 such that the face of the meter follows the incline of surface 21 and the upper surface of the sensing means follows the incline of the surface 10. Additionally, it has been found preferable for easiest operation of the apparatus to incline the meter face at an angle of approximately 138° measured clockwise from the upper surface of the portion 3, to incline the upper lens surface of the sensing means at an angle of approximately 147° measured counterclockwise from the meter face and to incline the rearward most wall of the housing portion 4 opposite the surface 21 at an angle of approximately 10° measured counterclockwise from the upper lens surface of the sensing means.

It should be also pointed out that while the apparatus of FIG. 1 has been specifically illustrated in terms of a means for sensing light and water conditions of a plant, it could be readily modified by suitable calibration and the suitable changing of the sensing means to measure either light and or water conditions. Thus, it is apparent that the invention is intended to extend to the use of a common meter and selective coupling means with each of the different combinations of sensing means disclosed.

In all cases, it is understood that the above described arrangements are merely illustrative of the many possible specific embodiments which represent applications of the present invention. Numerous and varied other arrangements can be readily devised in accordance with the principles of the present invention without departing from the spirit and scope of the invention. Thus, for example, the disclosed apparatus configurations can be employed in connection with determining conditions related to a lawn or a garden, as well as conditions related to house plants.

What is claimed is:
 1. An apparatus for determining the conditions related to a plant comprising:
  a first sensing means for generating a first electrical signal corresponding to a first condition related to said plant;

a second sensing means for generating a second electrical signal corresponding to a second condition related to said plant;

an indication means comprising a common galvanic meter;

a coupling means for selectively coupling said first and second signals to said galvanic meter, whereby said galvanic meter is made selectively responsive to said first and second signals and selectively converts said first and second signals into indications of said first and second conditions, respectively;

a first reference source for relating said indication of said first condition to a first preselected reference for said first condition;

and a second reference source for relating said indication of said second condition to second preselected reference for said second condition.

2. Apparatus in accordance with claim 1 in which said coupling means includes a switch for selectively connecting said first and second sensing means to said galvanic meter and in which said meter has first and second calibrated scales for providing said indications of said first and second conditions, respectively.

3. Apparatus in accordance with claim 1 in which:
said first condition is the level of light in the vicinity of said plant;
said first preselected reference corresponds to a preselected level of light for said plant;
said second condition is the amount of water in the soil of said plant;
and said second preselected reference corresponds to a preselected amount of water for the soil of said plant.

4. Apparatus in accordance with claim 3 in which:
said second sensing means includes a slender probe comprised of dissimilar metals which when inserted into the soil of a plant generates an electrical current through voltaic electrolytic action which is related to the amount of water in said soil;
and said second electrical signal comprises said generated current.

5. Apparatus in accordance with claim 4 further comprising:
a housing for housing said first and second sensing means and said indication means, said housing comprising: a thin longitudinally extending bottom portion adapted to be gripped by a user of said apparatus, said bottom portion having an aperture extending throughout its length for supportively holding and storing said probe; and an upwardly extending portion disposed at one end of said bottom portion, said upwardly extending portion having a top surface in which is disposed an aperture for coupling light into said housing and onto said first sensing means.

6. Apparatus in accordance with claim 5 further including a pressable knob disposed on the said thin bottom portion for operating said switch.

7. Apparatus in accordance with claim 5 in which:
said upwardly extending portion has a slanted side wall extending between the upper surface of said bottom portion and said top surface, said slanted sidewall having an aperture;

and said galvanic meter includes a scale and is arranged in said housing such that said scale is adjacent said slanted sidewall and viewable through the aperture thereof.

8. Apparatus in accordance with claim 7 wherein:
said top surface of said upwardly extending portion is slanted relative to said upper surface of said bottom portion;
and said first sensing means is arranged in said upwardly extending portion so as to have a surface thereof adjacent said aperture of said top surface.

9. Apparatus in accordance with claim 8 wherein:
said slanted sidewall is inclined at an angle of approximately 138° measured clockwise from said upper surface;
and said slanted top surface is inclined at an angle of approximately 147° measured clockwise from said slanted sidewall.

10. Apparatus in accordance with claim 9 wherein:
said first sensing means includes:
a photocell
a calibration wedge disposed in front of said photocell;
a color correction filter arranged in front of said wedge;
and a cosine correction lens disposed in front of said filter.

11. Apparatus in accordance with claim 1 in which:
said first condition is the amount of water in the soil of said plant;
said first preselected reference corresponds to a preselected amount of water for the soil of said plant;
said second condition is the pH level of the water in the soil of said plant;
and said second preselected reference corresponds to a preselected pH level for the water in the soil of said plant.

12. A method for determining conditions related to a plant comprising the steps of:
placing adjacent said plant one of first and second sensing means, said first and second sensing means when placed adjacent said plant generating respective first and second electrical signals corresponding to first and second conditions related to said plant; selectively connecting said first and second sensing means to a common galvanic meter of an indication means for converting said first signal to an indication of said first condition when said first sensing means is connected to said galvanic meter and for converting said second signal to an indication of said second condition when said second sensing means is connected to said galvanic meter; and comparing said indication to a first reference corresponding to a preselected reference for said first condition when said indication is generated by converting said first signal and to a second reference corresponding to a preselected reference for said second condition when said indication is generated by converting said second signal.

13. A method in accordance with claim 17 in which:
said first condition is the level of light in the vicinity of said plant; and
said second condition is the amount of water in the soil of said plant.

* * * * *